(12) United States Patent
Kondo et al.

(10) Patent No.: US 6,778,998 B2
(45) Date of Patent: Aug. 17, 2004

(54) SIGNAL ACQUIRING APPARATUS, DATABASE, DATABASE SYSTEM, SIGNAL PRESENTING SYSTEM, AND SIGNAL ACQUIRING, STORING, AND PRESENTING SYSTEM

(75) Inventors: Tetsujiro Kondo, Tokyo (JP); Hideo Nakaya, Kanagawa (JP)

(73) Assignee: Sony Corporation, Tokyo (JP)

( * ) Notice: Subject to any disclaimer, the term of this patent is extended or adjusted under 35 U.S.C. 154(b) by 122 days.

(21) Appl. No.: 09/970,567

(22) Filed: Oct. 4, 2001

(65) Prior Publication Data

US 2002/0069211 A1 Jun. 6, 2002

(30) Foreign Application Priority Data

Oct. 5, 2000 (JP) .................................... 2000-306792

(51) Int. Cl.[7] .............................................. G06F 17/30
(52) U.S. Cl. ...................................... 707/104.1; 707/10
(58) Field of Search .............................. 707/102, 104.1; 340/573.1, 605, 870.11; 382/115; 600/300, 301, 528, 544; 604/66, 67

(56) References Cited

U.S. PATENT DOCUMENTS 5,557,263 A * 9/1996 Fisher et al. ................. 340/605
6,084,516 A * 7/2000 Yasushi et al. .............. 340/573.1
6,241,288 B1 * 6/2001 Bergenek et al. ............. 283/67

* cited by examiner

Primary Examiner—Diane D. Mizrahi
Assistant Examiner—Apu M Mofiz
(74) Attorney, Agent, or Firm—Frommer Lawrence & Haug LLP; William S. Frommer

(57) ABSTRACT

A re-experience with enhanced realism is achieved by storing audiovisual signals and bio-signals as experience information. A signal acquirer/encoder collects the audiovisual information and bio-information regarding a user through a plurality of sensors attached to the user, integrates and encodes these signals, and stores the integrated and encoded signals. A storage selects effective information from the integrated signals on the basis of a comprehensive judgment, and stores the effective information. The storage is connected to a rental integrated database that includes a personal database allotted to each user. The user stores enciphered integrated signals in the database allotted to the user. The database is connected to a public database to automatically access associated information. The database and an integrated signal presenter are connected, enabling the user to have a re-experience by means of the integrated signal presenter.

19 Claims, 16 Drawing Sheets

FIG. 3
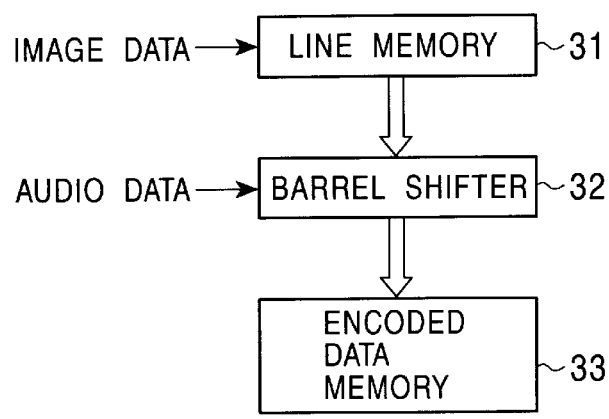
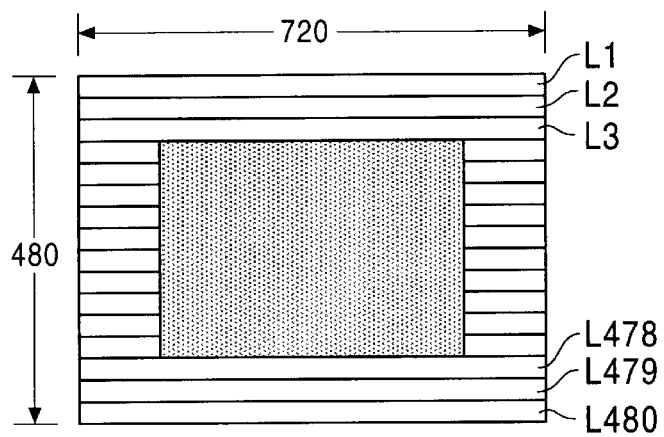
FIG. 4A
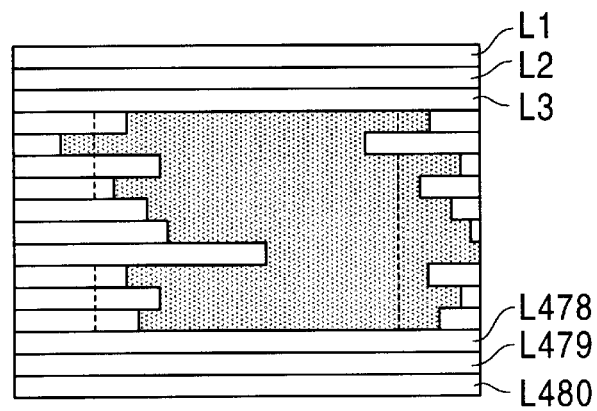
FIG. 4B

FIG. 15

| ATTRIBUTE DATA | |
|---|---|
| PERSONAL ID | ~100a |
| EVENT NAME | ~100b |
| TIME STAMP | ~100c |
| LOCATION | ~100d |
| LINK DESTINATION 1 | ~100e |
| LINK DESTINATION 2 | ~100f |

FIG. 16

| ATTRIBUTE DATA | |
|---|---|
| TOKKYO TARO | ~100a |
| WATCHING THE OPENING CEREMONY OF SYDNEY OLYMPIC | ~100b |
| 10:00AM SEPT. 15, 2000 | ~100c |
| OLYMPIC STADIUM | ~100d |
| ABC BROADCAST MATERIAL NO. ??? | ~100e |
| NNS BROADCAST MATERIAL NO. XXX | ~100f |

SIGNAL ACQUIRING APPARATUS, DATABASE, DATABASE SYSTEM, SIGNAL PRESENTING SYSTEM, AND SIGNAL ACQUIRING, STORING, AND PRESENTING SYSTEM

BACKGROUND OF THE INVENTION

1. Field of the Invention

The present invention relates to a signal acquiring apparatus, a database, a database system, a signal presenting system, and a signal acquiring, storing, and presenting system that are applied for storing audiovisual information and bio-information regarding an event experienced by an individual.

2. Description of the Related Art

With the increasing amount of digital information, such as digital image information, owned by individuals, services for storing the digital information of each individual are becoming commercially practical. There have been proposed a service that allows an individual to easily prepare his or her own history, i.e., a personal history, (see the Japanese Unexamined Patent Publication No. 11-66049) rather than simply storing data. According to the system for creating a personal history described in the literature, a user's terminal and a manager or server computer are connected through the intermediary of the Internet, and the manager is provided with a group of databases. The group of databases includes a user database for user management, a personal event database, a historical event database, an event selection database, and a chronological database. A user starts up a WWW browser at his or her terminal, and uses the above-mentioned database information to effect processing to prepare a chronology as his or her personal history. The provision of the historical event database enables the user to select history events that he or she wishes to relate to his or her personal events, thus contributing to easier preparation of the personal history.

According to the literature mentioned above, however, the information regarding personal events has been character-oriented and the associated image and audio information has not been the information regarding users' own experiences of seeing or hearing. Hence, the information regarding personal events has no significant difference from that presented by an electronic album except that it is composed as a chronology. In addition, the information has been inadequate in reproducing the experiences of a user later. There has been another disadvantage in that the manager is equipped with the databases, so that cost, including the cost for creating and managing databases, is required.

SUMMARY OF THE INVENTION

Accordingly, it is an object of the present invention to provide a signal acquiring apparatus, a database, a database system, a signal presenting system, and a system for acquiring, storing, and presenting signals that make it possible to store the audiovisual information regarding an audiovisual experience that a user has had, and the bio-information regarding the user, to reproduce the user's experiences later, and to accomplish a good stock of information by utilizing publicly available databases.

To this end, according to a first aspect of the present invention, there is provided a signal acquiring apparatus equipped with a plurality of sensors attached to a person, detecting devices for generating detection signals from the plurality of sensors, a selecting device for automatically selecting detection signals containing effective information from among the plurality of detection signals, and a storing device for storing the selected detection signals.

According to a second aspect of the present invention, there is provided a database equipped with a device for receiving the detection signals that are generated from each of the plurality of sensors attached to a user and stored in a storing device, a device of database for each person in which received detection signals are stored for each user, a communication device that is connected to an external database to access information in another database associated with the stored detection signals, and a device for acquiring associated information from another database via the communication device.

According to a third aspect of the present invention, there is provided a database system equipped with a signal acquiring apparatus that includes a plurality of sensors attached to a person, a detecting device for generating detection signals from the plurality of sensors, a selecting device for automatically selecting detection signals containing effective information from among the plurality of detection signals, and a storing device for storing the selected detection signals, and a database connected to the signal acquiring apparatus via a communication device, wherein the database includes a device for receiving detection signals from the signal acquiring apparatus and a device for database for each person in which received detection signals are stored for each user.

Accordingly to a fourth aspect of the present invention, there is provided a signal presenting system that includes a database equipped with a device for receiving detection signals that are generated by each of a plurality of sensors attached to a user and stored at a storing device, and a device of database for each person in which received detection signals are stored for each user, and a signal presenting apparatus connected to the database via a communication device, wherein the signal presenting apparatus includes a device for receiving detection signals from the database via the communication device and a device for reproducing an environment on the basis of the detection signals.

According to a fifth aspect of the present invention, there is provided a signal acquiring, storing, and presenting system that includes a signal acquiring apparatus that has a plurality of sensors attached to a person, a detecting device for generating detection signals from the plurality of sensors, a selecting device for automatically selecting detection signals containing effective information from among the plurality of detection signals, and a storing device for storing the selected detection signals, a database including a device that is connected to the signal acquiring apparatus via a first communication device to receive detection signals from the signal acquiring apparatus and a device of database for each person in which the received detection signals are stored for each user, and a signal presenting apparatus including a device that is connected to the database via a second communication device to receive detection signals from the database, and a device for reproducing an environment on the basis of the detection signals.

According to a sixth aspect of the present invention, there is provided a signal acquiring, storing, and presenting system including a first manager that manufactures and/or markets a signal acquiring apparatus having a plurality of sensors attached to a person, a detecting device for generating detection signals from the plurality of sensors, a selecting device for automatically selecting detection signals containing effective information from among the plurality of detection signals, and a storing device for storing the selected detection signals, a second manager that manages a database including a device that is connected to the signal acquiring apparatus via a first communication device to receive detection signals from the signal acquiring apparatus and a device of database for each person in which the received detection signals are stored for each user, and a third manager that manages a signal presenting apparatus including a device that is connected to the database via a second communication device to receive detection signals from the database, and a device for reproducing an environment on the basis of the detection signals.

According to the present invention, the signal acquiring apparatus makes it possible to acquire audiovisual signals and bio-signals obtained from user's actual experiences, to selectively store impressive signals among the aforementioned signals, and to store such signals also in a database. Furthermore, since audiovisual signals and bio-signals are stored in a database, reproduction including sensory effect can be accomplished during a re-experience. The signal presenting apparatus permits a re-experience with highly realistic sensations to be achieved. Moreover, according to the present invention, associated information can be acquired from an external database in addition to the data acquired by an individual so as to supplement the contents of a database, thus achieving a high-quality database having a good stock of information.

BRIEF DESCRIPTION OF THE DRAWINGS

FIG. 3 is a block diagram showing an example of an encoder that can be used in the present invention;

FIGS. 4A and 4B are diagrams used to describe encoding;

FIG. 15 is a schematic diagram illustrating the format of attribute data in the embodiment of the present invention;

FIG. 16 is a schematic diagram for describing a specific example of the attribute data;

DESCRIPTION OF THE PREFERRED EMBODIMENTS

Figure 1:
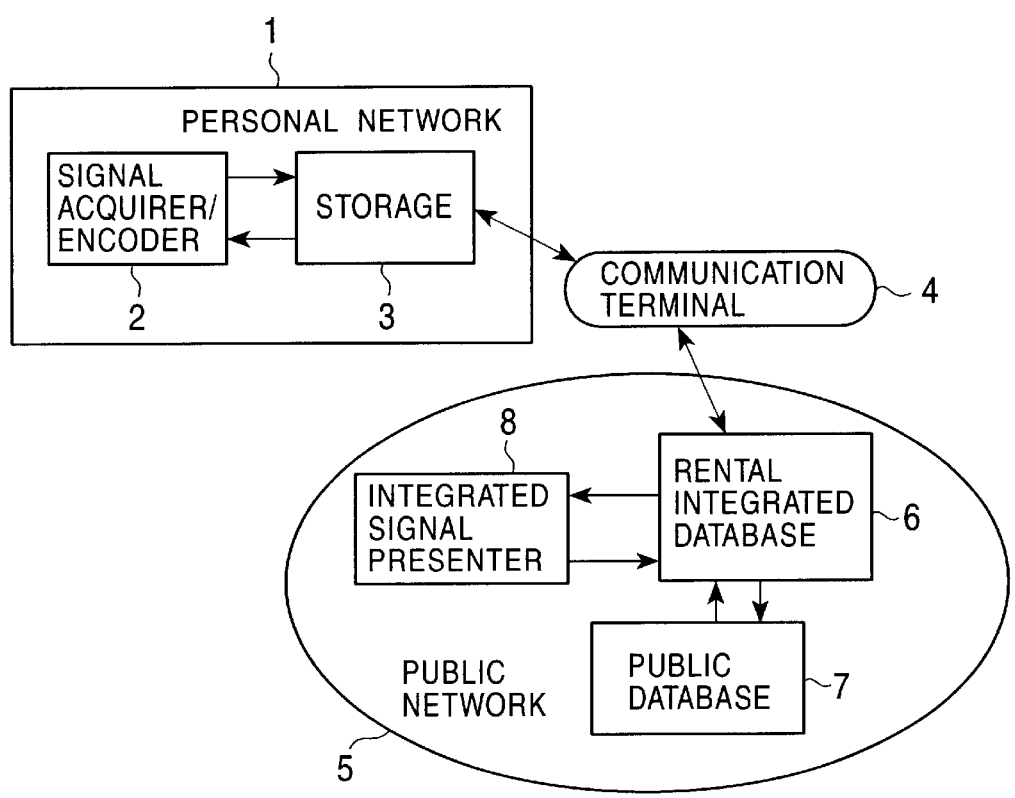
FIG. 1 is a block diagram showing an outline of an entire system according to an embodiment of the present invention

An embodiment in accordance with the present invention will now be described. Referring first to FIG. 1, the schematic configuration of a signal acquiring, storing, and presenting system will be described. A signal acquiring unit 1 for each individual or user has a signal acquirer/encoder 2 and a storage 3. The signal acquirer/encoder 2 gathers audiovisual information and bio-information regarding a user from a plurality of sensors attached to the user, and integrates and encodes the gathered signals. The integrated and encoded signals will be referred to as "integrated signals." The signal acquirer/encoder 2 is designed to be portable, that is, "a mobile terminal" so as to allow a user thereof to carry it. The integrated signals are stored in a removable storing medium, such as a card-shaped semiconductor memory.

The storage 3 can be implemented by, for example, a personal computer installed at a user's home. A storing medium is inserted in the storage 3, and the integrated signals are read out from the storing medium. The storage 3 selects effective information from the integrated signals according to a comprehensive judgment, and temporarily stores the selected effective information in a storing medium, such as a hard disk. Alternatively, the integrated signals may be transmitted from the signal acquirer/encoder 2 to the storage 3 by wired or wireless communication rather than using the storing medium. Thus, the signal acquirer/encoder 2 and the storage 3 are connected through a personal network.

The signal acquiring unit 1 (the storage 3) is connected to a rental integrated database 6 through the intermediary of a communication terminal 4 and a public network 5. The communication terminal 4 is either a wired type or a wireless type. The integrated signals are enciphered to ensure security prior to transmission. The rental integrated database 6 includes a predetermined amount of database for each person that is assigned to each user. A user verifies the connection of communication by a particular authenticating means from the communication terminal 4, and transmits the enciphered integrated signals to the rental integrated database 6 to store the integrated signals in a database portion assigned to the user. The stored data include the transmitted enciphered integrated signals and attribute data. A company managing the rental integrated database 6 engages in the management of the stored data by concluding individual contracts with a plurality of users. The company runs the rental integrated database 6 by collecting from the users rental fees charged on the basis of, for example, contract terms or the amount of data.

The rental integrated database 6 is connected with diverse public databases 7 and automatically linked to associated information by a method to be discussed hereinafter. The public databases 7 means accessible databases, and accessing the databases may be either charged or free of charge. The rental integrated database 6 is also connected to an integrated signal presenter 8. The integrated signal presenter 8 is installed at a re-experience center, so that a user may have a re-experience by means of the integrated signal presenter 8 when the user wishes to enjoy a past experience again.

The system shown in FIG. 1 is actually run by a plurality of companies in many cases. Profits can be obtained by manufacturing and marketing the signal acquirer/encoder 2. Similarly, profits can be obtained by manufacturing and marketing the hardware or software of the storage 3. Furthermore, rental fees can be obtained according to the contract with the use of the rental integrated database 6. When the rental integrated database 6 is linked to the public database 7, the information fee will be paid to a company managing the public database 7. Service fees can be obtained by providing re-experiences by using the integral signal presenter 8. It is practical for the system to be operated by a plurality of companies since the system enables business profits to be obtained as mentioned above.

Figure 2:
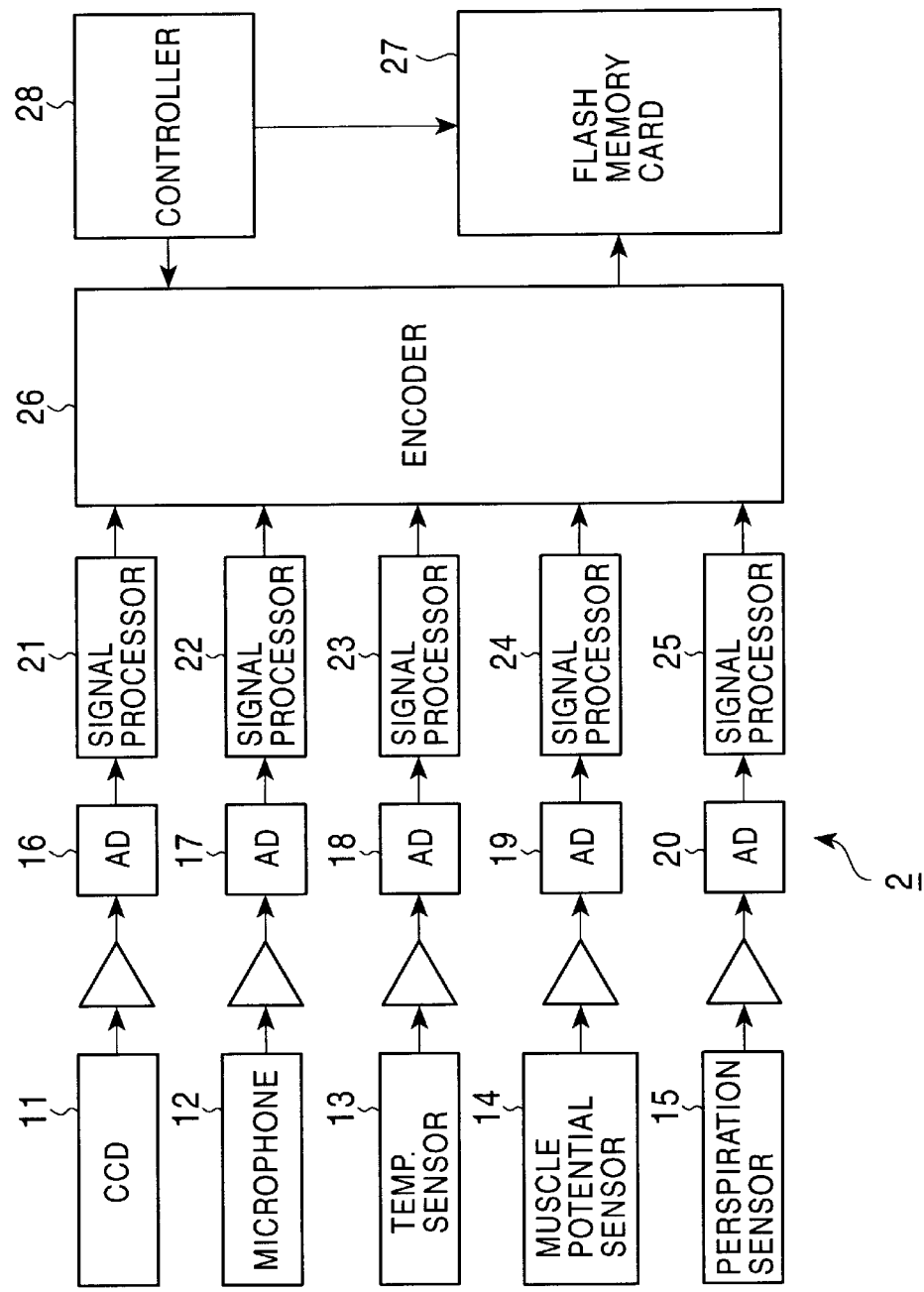
FIG. 2 is a block diagram showing an example of a signal acquirer/encoder in the embodiment of the present invention.

The constituents making up the foregoing system will be described in more detail. First, an example of the signal acquirer/encoder 2 of the signal acquiring unit 1 will be described with reference to FIG. 2. The signal acquirer/encoder 2 includes an image input section 11 using a CCD or the like, an audio input section 12 using a microphone, a temperature sensor 13 for measuring body temperatures, a muscle potential sensor 14 for detecting muscle potentials, and a perspiration sensor 15 for detecting perspiration so as to acquire audiovisual signals and bio-signals. The signal acquirer/encoder 2 may be provided with another sensor for inputting more bio-information, such as heart beats or blood pressures, other than the sensors shown in the drawing.

The sensors are attached to a user. For instance, the image input section 11, namely, the CCD, is attached to the frame or the like of glasses of a user to allow the CCD to generate image signals for images that are as close to the images actually perceived by the user as possible. Preferably, the CCD permits wide-angle shooting. Other sensors, including the microphone, may be attached to the frame of the glasses.

The output signals of the above input section and the sensors are supplied, through the intermediary of an amplifier, to A/D converters 16, 17, 18, 19, and 20 whereby to be converted into digital signals. The digital signals from the A/D converters 16 through 20 are supplied to signal processors 21, 22, 23, 24, and 25, respectively. The signal processors 21 through 25 individually carry out optimum noise reduction processing or the like thereby to remove unwanted signal components, such as noises, and also convert or shape them into signals that can be easily processed. The signals output from the signal processors 21 through 25 are encoded and converted into integrated signals by an encoder 26, and recorded as the signals of one sequence in a removable storing medium, such as a flash memory card 27. A controller 28 primarily controls the operation for writing the integrated signals from the encoder 26 to the flash memory card 27, and the operation for reading the integrated signals from the flash memory card 27.

FIG. 3 shows an example of the encoder 26. The aforesaid images and sounds, and various bio-signals respectively exhibit physical characteristics. For example, images are characterized in that local correlation increased in spatial and temporal directions. Image data provides the largest amount of information; therefore, another data is embedded in image data to effect integrated encoding so as to control an increase in the amount of information. FIG. 3 exemplifies the configuration of the encoder for embedding, for example, audio data, in image data.

The image data, which has been obtained at a sampling frequency of 13.5 MHz and quantized to 8 bits per pixel, is supplied to a line memory 31. The image data has 720 pixels in the horizontal direction and 480 lines in the vertical direction, and 30 frames per second in the temporal direction. One line of image data stored in the line memory 31 is supplied in parallel to a barrel shifter 32. An output of the barrel shifter 32 is stored at an encoded data memory 33.

Furthermore, audio data is supplied to the barrel shifter 32 as a signal for controlling a shifting amount. The audio data has the same sampling frequency as a line frequency, namely, 15.7 kHz, and 9 bits per sample. This means that one sample of the audio data occurs for each line of image. The barrel shifting means an annular shifting operation.

FIG. 4A illustrates a simple example of one frame of image data, namely, an original image having a rectangular dark central portion in one image. The image has lines, L1, L2, L3, . . . , L478, L479, and L480, L1 being the topmost line. Each line has 720 samples in the horizontal direction. The drawing, however, shows much fewer lines than 480 lines for simplicity.

The value of audio data in which one sample occurs per line varies from 0 to 511. Based on the value of the audio data, the data of each line of an image is horizontally barrel-shifted to the right. The data of the first line L1 or the lines located at predetermined intervals are not subjected to the barrel shifting, and the image data of the lines that are not subjected to the barrel shifting will be used as the reference data for decoding. If the image data of a line has exactly the same value as in the case of lines L2, L3, L478, L479, and L480, then the data remains unchanged after barrel shifting, thus making these lines unsuited for encoding.

FIG. 4B illustrates the image data obtained by shifting the lines in the image of FIG. 4A by audio data. The image data, which is integrated data, is stored at the encoded data memory 33. The flash memory card 27 shown in FIG. 2 corresponds to the encoded data memory 33. As shown in FIG. 4B, the data has been encoded so that the vertical continuity is disturbed by the audio data without causing an increase in the information amount of the image data and while retaining the horizontal continuity of the image.

Figure 5:
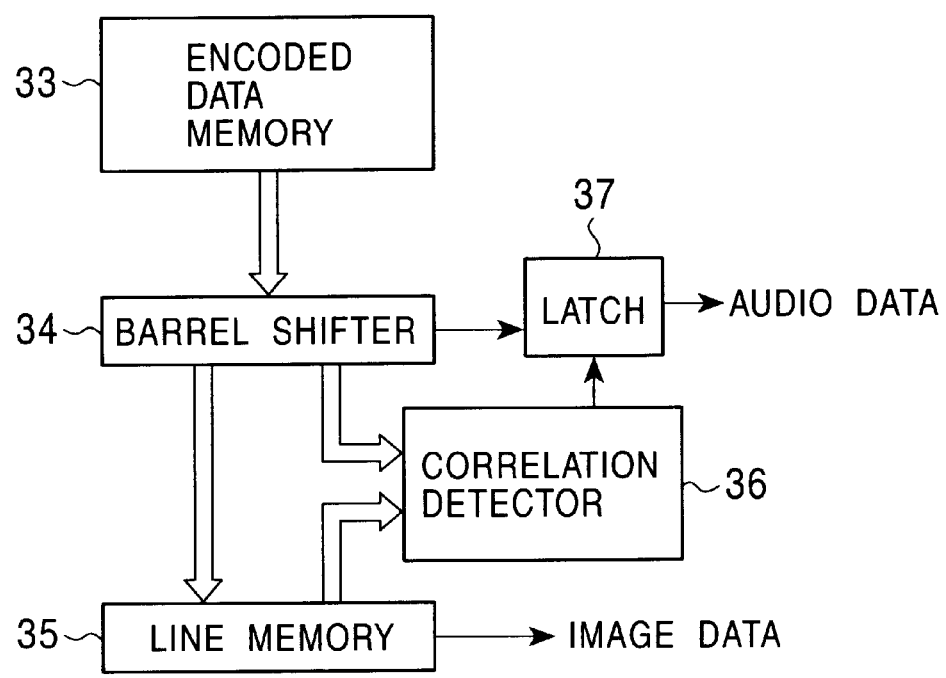
FIG. 5 is a block diagram showing an example of a decoder.

FIG. 5 shows an example of a decoder. The integrated and encoded image data has been stored in the encoded data memory 33. One line of data read from the encoded data memory 33 is supplied to a barrel shifter 34. An output of the barrel shifter 34 is supplied to a line memory 35 and a correlation detector 36. The line memory 35 stores the data of the first line L1 as the initial value. The image data of the barrel shifter 34 is encoded data, while the data stored in the line memory 35 is the decoded image data of one line before.

An output of the barrel shifter 34 and an output of the line memory 35 are supplied to the correlation detector 36. The correlation observed between one line of data of the barrel shifter 34 and one line of data of the line memory 35, i.e., the correlation in the vertical direction, when the shifting amount of the barrel shifter 34 is changed from 0 to 1, 2, . . . , 511 is computed to detect the shifting amount at which a maximum vertical correlation is obtained. The image data that has been decoded is output from the line memory 35. The shifting amount of the barrel shifter 34 is supplied to a latch 37. A latch pulse generated when the correlation detector 36 detects a maximum correlation is supplied to the latch 37, and the shifting amount at which the maximum correlation is obtained is captured into the latch 37. The latch 37 outputs audio data. The integrating and encoding described above is merely an example; as an alternative, the embedded encoding disclosed in Japanese Unexamined Patent Publication No. 2000-59743 may be used.

Figure 6:
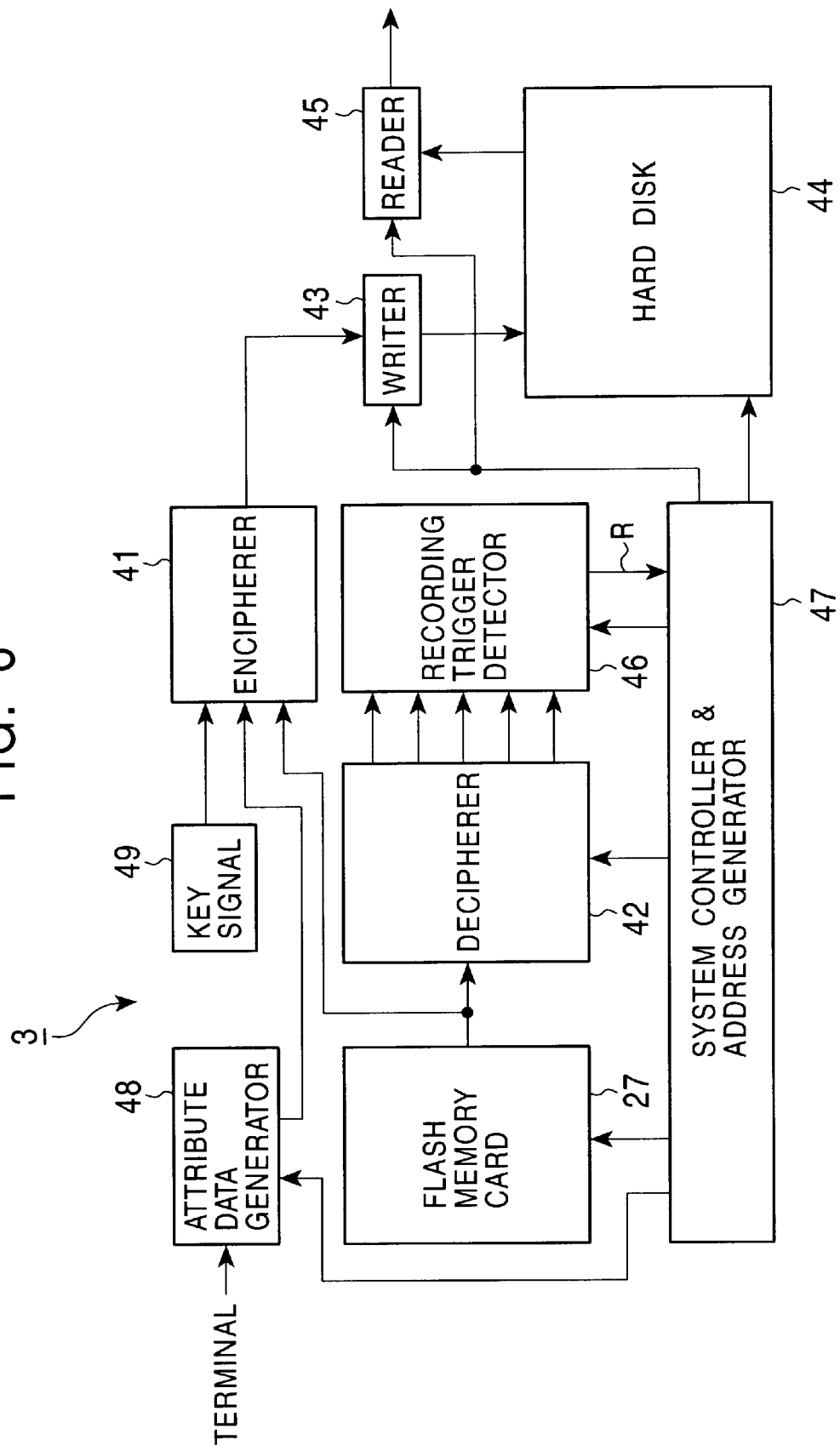
FIG. 6 is a block diagram showing an example of a storage in a signal acquiring apparatus according to an embodiment of the present invention.

FIG. 6 shows the configuration, which is an example, of the storage 3 of the signal acquiring unit 1. In the storage 3, the integrated signals read from the flash memory card 27 are supplied to an encipherer 41 and a decipherer 42. The integrated signals that have been enciphered by the encipherer 41 are stored in a hard disk 44 through the intermediary of a writer 43. Stored signals are read from the hard disk 44 through the intermediary of a reader 45. The hard disk is a mere example of a storing medium; alternatively, a different storing medium, such as an optical disc, a magnetic tape, or a semiconductor memory, may be used.

The integrated signals read from the flash memory card 27 are deciphered by the decipherer 42. From the decipherer 42, image signals, audio signals, body temperature signals, muscle potential signals, and perspiration signals are separately obtained. These somesthetic signals, namely, audiovisual signals and bio-signals, are supplied to a recording trigger detector 46. The recording trigger detector 46 generates a trigger signal R that indicates whether the received somesthetic signals are to be recorded in the hard disk 44, and supplies the trigger signal R to a system controller & address generator 47. As it will be discussed hereinafter, whether somesthetic signals are the effective ones to be recorded in the hard disk 44 is comprehensively determined on the basis of a plurality of somesthetic signals. By using the trigger signal R, the audiovisual signals representing the experiences that have impressed a user can be selected and recorded in the hard disk 44.

The system controller & address generator 47 controls the entire processing of the storage 3. Based on the aforesaid trigger signal R, the system controller & address generator 47 controls the addresses at which integrated signals from the flash memory card 27 are read out, and reads out the integrated signals that have been determined to be effective. The read integrated signals are enciphered by the encipherer 41, and written to the hard disk 44 through the intermediary of the writer 43. The writer 43 and the hard disk 44 are controlled by the system controller & address generator 47. The system controller & address generator 47 also controls the operation for reading from the hard disk 44. Read signals are output through the intermediary of the reader 45.

As soon as the integrated signals to be recorded are decided by the recording trigger detector 46, control is conducted so as to read the integrated signals from the flash memory card 27. A delay element for delaying integrated signals for a time required by the recording trigger detector 46 to decide on integrated signals to be recorded may be provided between the flash memory card 27 and the encipherer 41.

An attribute data generator 48 generates attribute data associated with integrated signals when a user operates a terminal, namely, the signal acquiring unit 1, thereby to enter desired attribute data. For instance, event names, such as an athletic meeting or Olympic, are used as the attribute data. The attribute data may also include the date, time and location related to the experiences of a user. The attribute data, which provides the keywords of experiences, will be explained hereinafter by using a specific example. The attribute data is also supplied to the encipherer 41.

The encipherer 41 receives the integrated signals read from the flash memory card 27 and the attribute data from the attribute data generator 48, and enciphers these integrated signals and attribute data by using a key signal 49 to protect privacy. For example, the bio-data, such as fingerprints or the like, for personal authentication that has been separately recorded is used as the key signal 49.

Figure 7:
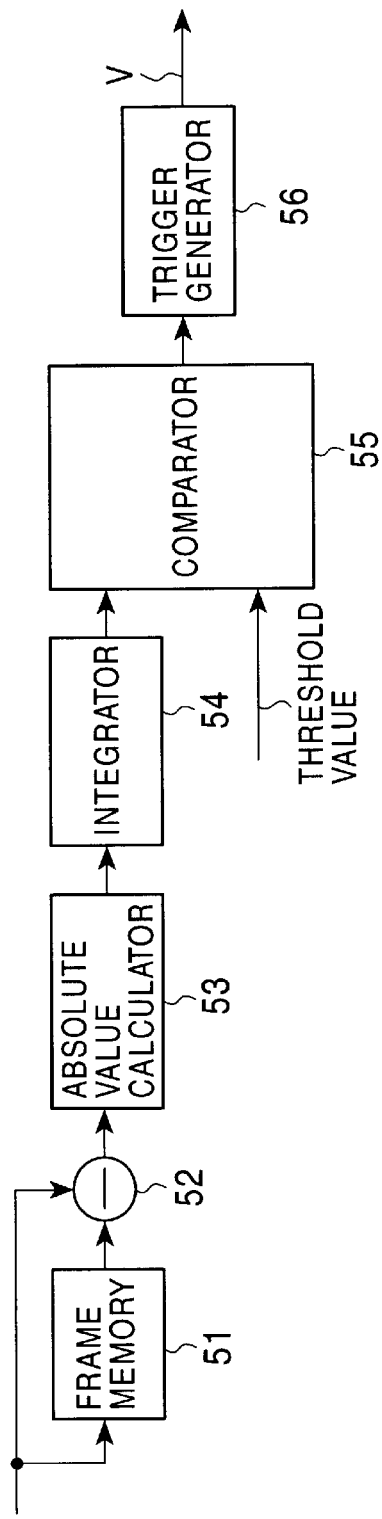
FIG. 7 is a block diagram used to describe a recording trigger detector in a storage.

An example of the recording trigger detector 46 shown in FIG. 6 will be described. FIG. 7 illustrates a configuration for processing image signals. A trigger signal V related to an image signal is created in the configuration shown in FIG. 7. Image signals from the decipherer 42 are supplied to a frame memory 51 and a subtractor 52, and the outputs of the frame memory 51 are supplied to the subtractor 52. The subtractor 52 calculates the difference between the supplied image signals, and supplies the calculated difference to an absolute value calculator 53. The absolute value calculator 53 calculates an absolute value on the supplied difference, and supplies the calculated absolute value of the difference to an integrator 54. The integrator 54 integrates the supplied absolute values of differences for a predetermined number of frames, and supplies the integrated value to a comparator 55.

A predetermined threshold value is supplied to the comparator 55, and a signal indicating the result of the comparison between the threshold value and an integrated value is supplied to a trigger generator 56. The trigger generator 56 generates the trigger signal V on the basis of the supplied signal. The trigger signal V is generated in such a case where an object in an image moves, a CCD moves together with a person wearing the CCD, or an entire luminance level changes. In any one of the cases, a decision can be made on the basis of the difference between frames. As an alternative, a motion vector may be extracted according to a block matching method or the like, and the processing based on the extracted motion vector may be carried out to generate a trigger signal.

Figure 8:
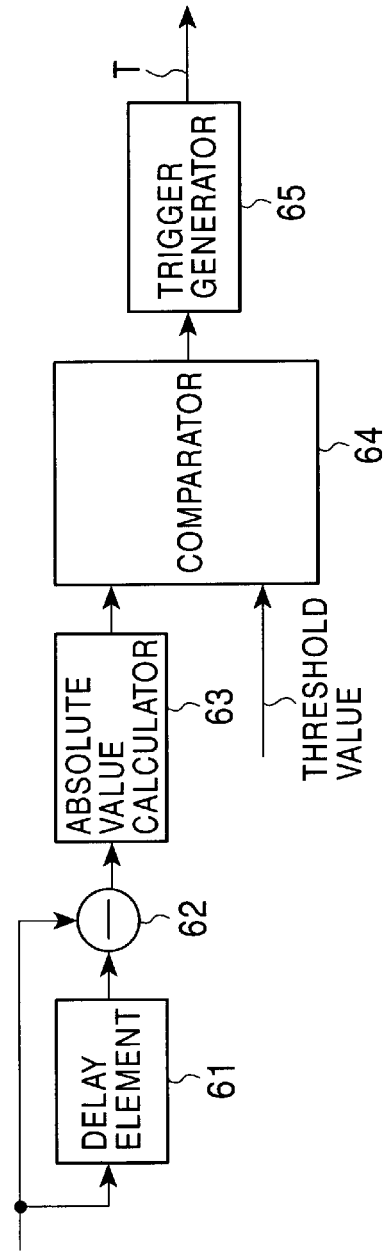
FIG. 8 is another block diagram used to describe the recording trigger detector in the storage.

FIG. 8 illustrates a configuration for generating a trigger signal T associated with a body temperature signal detected by a temperature sensor. Body temperature signals from the decipherer 42 are supplied to a delay element 61 and a subtractor 62. The delay element 61 delays supplied signals for a predetermined period of time before supplying the signals to the subtractor 62. The subtractor 62 calculates the difference between two supplied signals, and supplies the calculated difference to an absolute value calculator 63. The absolute value calculator 63 calculates an absolute value on the supplied difference, and supplies the calculated absolute value of the difference to a comparator 64.

A predetermined threshold value is supplied to the comparator 64, and a signal indicating the result of the comparison between the threshold value and an output of the absolute value calculator 63 is supplied to a trigger generator 65. The trigger generator 65 produces the trigger signal T on the basis of the supplied signal. Thus, the trigger signals are generated mainly when the body temperature of a wearer changes due to some stimulus applied to the wearer. The period of time retarded by the delay element 61 may be set to permit optimized detection of a change in the body temperature.

Figure 9:
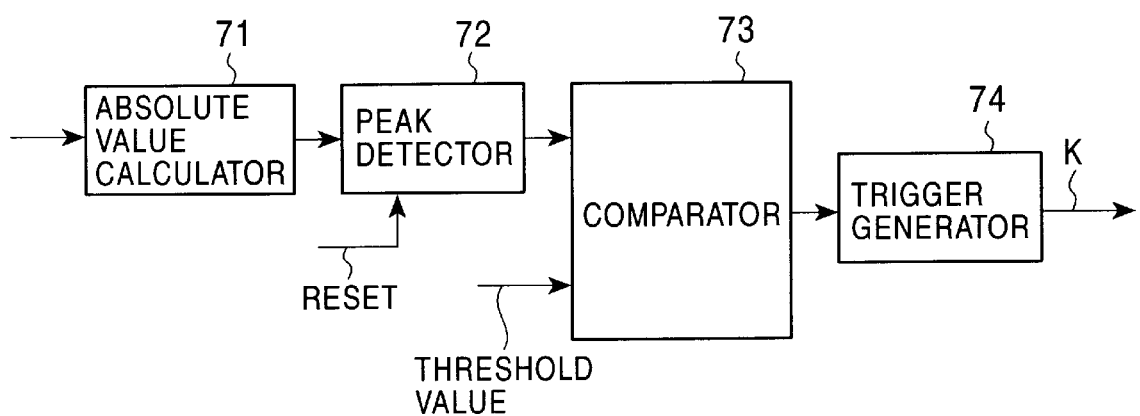
FIG. 9 is still another block diagram used to describe the recording trigger detector in the storage.

FIG. 9 shows a configuration for generating a trigger signal K associated with a muscle potential signal detected by a muscle potential sensor. A muscle potential signal from the decipherer 42 is supplied to an absolute value calculator 71, and an output of the absolute value calculator 71 is supplied to a peak detector 72. The peak detector 72 detects a peak value from the supplied signal, and supplies the detected peak value to a comparator 73. The peak detector 72 receives a reset signal at predetermined intervals.

Each time a reset signal is supplied, the peak value previously detected by the peak detector 72 is reset. Thus, peaks are detected at predetermined time intervals. A predetermined threshold value is supplied to the comparator 73, and a signal indicating the result of the comparison between the threshold value and an output of the peak detector 72 is supplied to a trigger generator 74. The trigger generator 74 produces the trigger signal K on the basis of the supplied signal. In this manner, whether the trigger signal K should be generated is decided at the predetermined time intervals.

Although not shown, a trigger signal H indicating a sudden increase in the amount of perspiration is also generated on the basis of a perspiration signal from a perspiration sensor.

With the arrangement described above, the trigger signals are generated mainly if a muscle potential significantly changes by a certain degree or more due to a stimulus applied to the wearer, or a motion or the like of the wearer. For instance, if the muscle potential sensor is attached to a facial muscle, then the trigger signals are generated as facial expression changes. The trigger signals may alternatively be generated by carrying out the processing based on the difference between pulse or peak intervals of a muscle potential.

Figure 10:
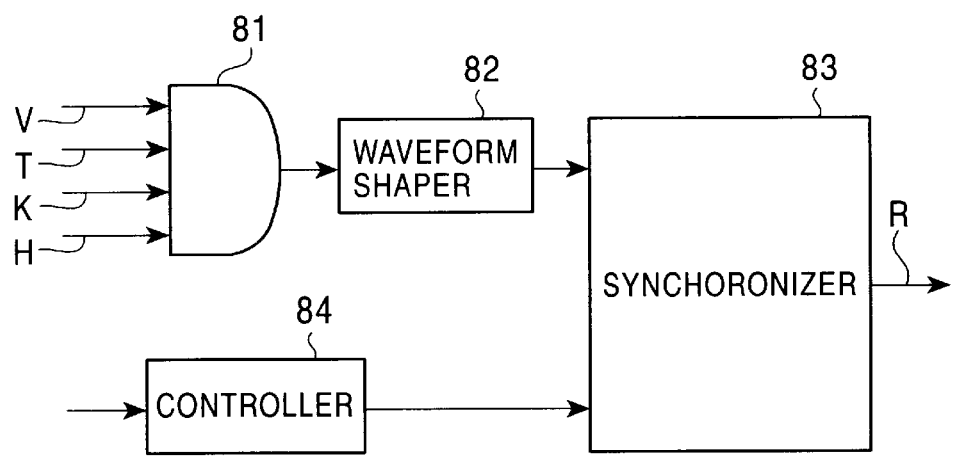
FIG. 10 is a further block diagram used to describe the recording trigger detector in the storage.

Furthermore, the recording trigger detector 46 makes a comprehensive judgment on the basis of the trigger signals produced as described above, and produces a signal R indicating a valid write period of time to store only effective somesthetic signals. An example of the configuration for making a comprehensive judgment is illustrated in FIG. 10, which shows a case where the aforesaid four different trigger signals V, T, K, and H are supplied as trigger signals. The trigger signals V, T, K, and H are supplied to an AND circuit 81. The AND circuit 81 generates an AND signal on the basis of the trigger signals V, T, K, and H, and supplies the generated AND signal to a waveform shaper 82. The waveform shaper 82 carries out waveform shaping on the supplied signal to primarily remove isolated points. An output of the waveform shaper 82 is supplied to a synchronizer 83.

A controller 84 generates a signal for synchronization information according to a command of the system controller & address generator 47, and supplies the generated signal to the synchronizer 83. In response to the signal output from the waveform shaper 82, the synchronizer 83 carries out processing to implement synchronization according to the command of the system controller & address generator 47. As a result of the processing, a signal R indicating a valid write period of time is output from the synchronizer 83. The signal R is supplied to the system controller & address generator 47 thereby to encipher an integrated signal indicating the valid write period of time, and the enciphered integrated signal is written to the hard disk 44. By the output signal R of the recording trigger detector 46 described above, those audiovisual signals that are sufficiently impressive to cause bio-changes to take place are selectively and automatically written to the hard disk 44. At the same time, the bio-signals are also written to the hard disk 44. The bio-signals are used to decide whether a user feels impressive, and are saved to permit re-experiences later.

Even if trigger signals include other than V, T, K, and H, or if the number of types of trigger signals is other than four, the signal R indicating which signals that should be written (the period of time is specified) can be generated by changing the types or the number of trigger signals supplied to the AND circuit 81 in the aforesaid configurations.

Figure 11:
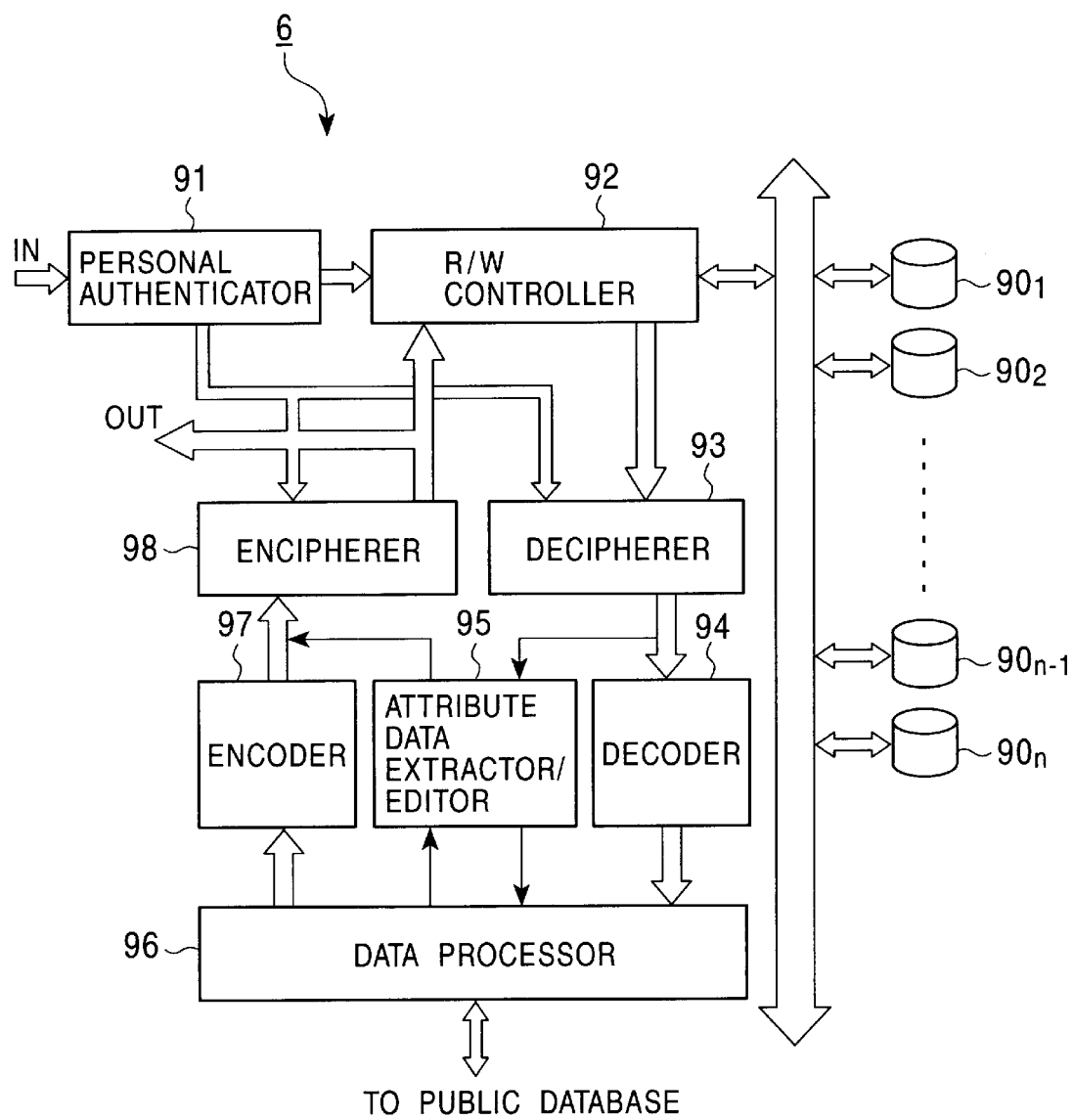
FIG. 11 is a block diagram showing an example of a rental integrated database in the embodiment of the present invention.

Referring now to FIG. 11, the rental integrated database 6 will be described. The enciphered integrated signals containing attribute data that have been stored in the hard disk 44 of the storage 3 of the signal acquiring unit 1 discussed above are applied to the rental integrated database 6 through the intermediary of the communication terminal 4 and the public network 5. As shown in FIG. 1, data can be input to or output from the integrated signal presenter 8 installed at a re-experience center, and the rental integrated database 6 can access the public database 7 to search desired data and downloads the acquired desired data.

The rental integrated database 6 is equipped with databases $90_1$ to $90_n$ rented out to each person. Users must be registered to obtain authorized access to the databases. Upon completion of the registration, a password or personal ID, for example, for authentication is issued. As an alternative, another type of information, such as the information regarding fingerprints, that makes it possible to identify the users, may be used. When a user attempts to register his or her attribute data and integrated signals in his or her database, authentication to verify the user is performed by a personal authenticator 91. When the authentication is cleared, enciphered attribute data and integrated signals are registered in the user's database by an R/W controller 92.

A company managing the rental integrated database 6 runs an automatic search and automatic linking program on the public network 5 thereby to search associated information on the basis of the attribute data registered in databases $90_1$ to $90_n$. Based on a search result, the information at a link destination is automatically written into attribute data. Furthermore, based on the information at the link destination in the attribute data, the company links to the public database 7 to acquire the data associated with the integrated signals already stored in the database of the rental integrated database 6 from the public database 7, and rewrites integrated signals that have been registered in the database.

To link to the public database 7 and acquire data and information therefrom, the rental integrated database 6 is provided with a decipherer 93, a decoder 94, an attribute data extractor/editor 95, a data processor 96 in charge of linking and editing, an encoder 97, and an encipherer 98. The data processor 96 also has a function for interfacing with the public database 7.

The integrated signals that have been read from a personal database and deciphered are supplied to the data processor 96. An extractor/editor 95 extracts attribute data, and the extracted attribute data is supplied to the data processor 96. The data processor 96 runs the automatic search and linking program on the public network 5 to search for information associated with attribute data. The database to which the searched information belongs is written into the attribute data as a link destination. The processing for writing the information to the link destination as the attribute data forms part of editing.

The associated information is downloaded to the data processor 96 from the public database 7 accessed on the basis of the information of the link destination. The data processor 96 checks for correlation between the deciphered integrated signals and the downloaded information to select only correlated data. The correlated data is recorded in the database through the intermediary of the encoder 97, the encipherer 98, and the R/W controller 92. In other words, some of the information in the database is rewritten by the associated information acquired from the public database 7.

Figure 12:
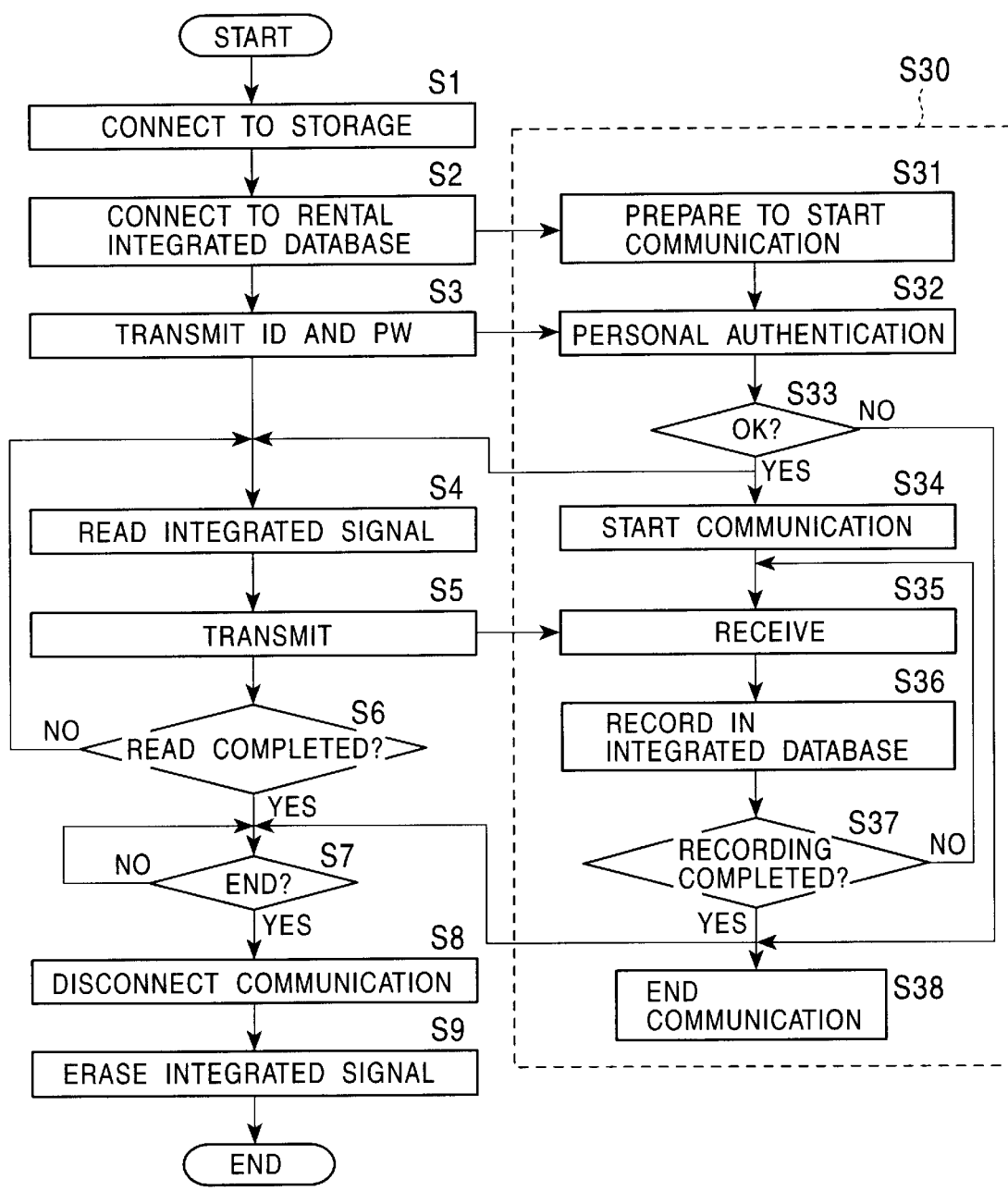
FIG. 12 is a flowchart for describing an example of the processing for transmitting data from the signal acquirer to the rental integrated database.

The procedure for transmitting data from the storage 3 of the signal acquiring unit 1 to the rental integrated database 6 will be described with reference to the flowchart shown in FIG. 12. The steps shown at left in FIG. 12 are included in the processing carried by the signal acquiring unit 1, while processing S30 at right enclosed by a dashed line includes the steps implemented in the rental integrated database 6. In step S1, connection to the storage 3 of the signal acquiring unit 1 is made, and in step S2, connection to the rental integrated database 6 is made. This establishes a communication path via the communication terminal 4.

In step S31, preparations for starting communication are made. A personal ID and a password are sent from the signal acquiring unit 1 to the rental integrated database 6. In step S32, personal authentication is performed. In step S33, it is determined whether the authentication has been successful. Upon successful authentication, communication is started in step S34, and an integrated signal is read from the storage 3 of the signal acquiring unit 1 in step S4. The read integrated signal is enciphered, and the enciphered integrated signal is transmitted in step S5. The enciphered integrated signal received in step S35 is recorded in the integrated database in step S36.

In step S6, the signal acquiring unit 1 monitors for the end of reading an integrated signal. Similarly, in step S37, the rental integrated database 6 monitors for the end of recording an integrated signal in the integrated database. As soon as reading is terminated, the communication is terminated in step S38. In step S7, whether both operations have been terminated is determined, and if the determination result is affirmative in step S7, then the communication is cut off in step S8. Then, in order to protect the confidentiality of data, the transmitted integrated signal is deleted from the stored contents of the storage 3.

Figure 13:
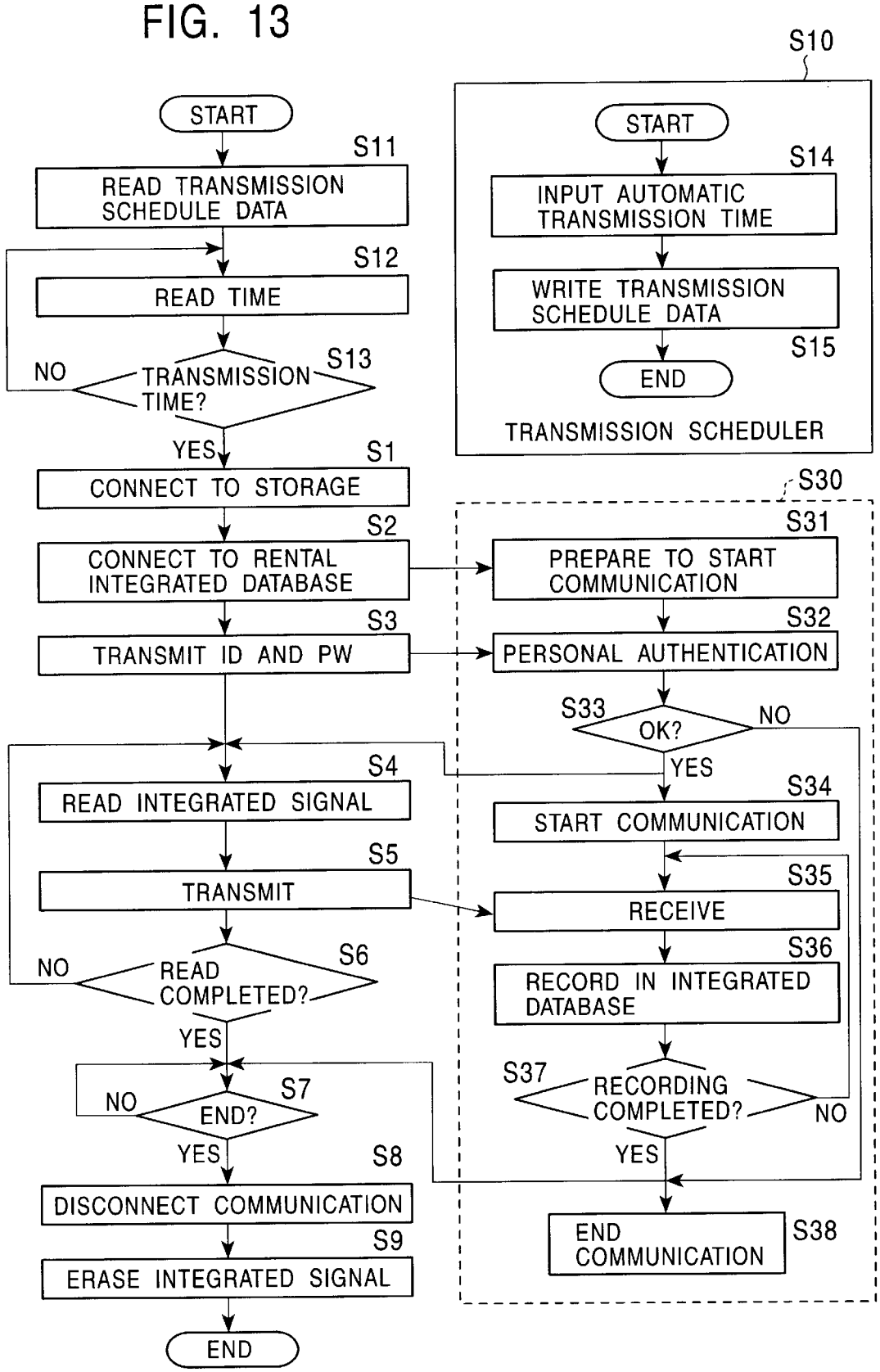
FIG. 13 is a flowchart for describing another example of the processing for transmitting data from the signal acquirer to the rental integrated database.

FIG. 13 shows another example of the flowchart illustrating the procedure for transmitting data from the signal acquiring unit 1 to the rental integrated database 6. The transmission is automatically accomplished by a timer of the communication terminal 4. First, transmission schedule data, which is created in step S10 of a transmission scheduler, is read in step S11. More specifically, automatic transmission time is input in step S14, and the transmission schedule data is read in step S15.

In step S12, the current time is read. In step S13, it is determined whether the current time coincides with the automatic transmission time, and if the determination result is affirmative, then the connection to the storage 3 is made (step S1). The communication processing thereafter is the same as the transmission processing described in conjunction with FIG. 12; hence, the same reference numerals will be assigned to the corresponding processing steps, omitting detailed descriptions thereof.

Figure 14:
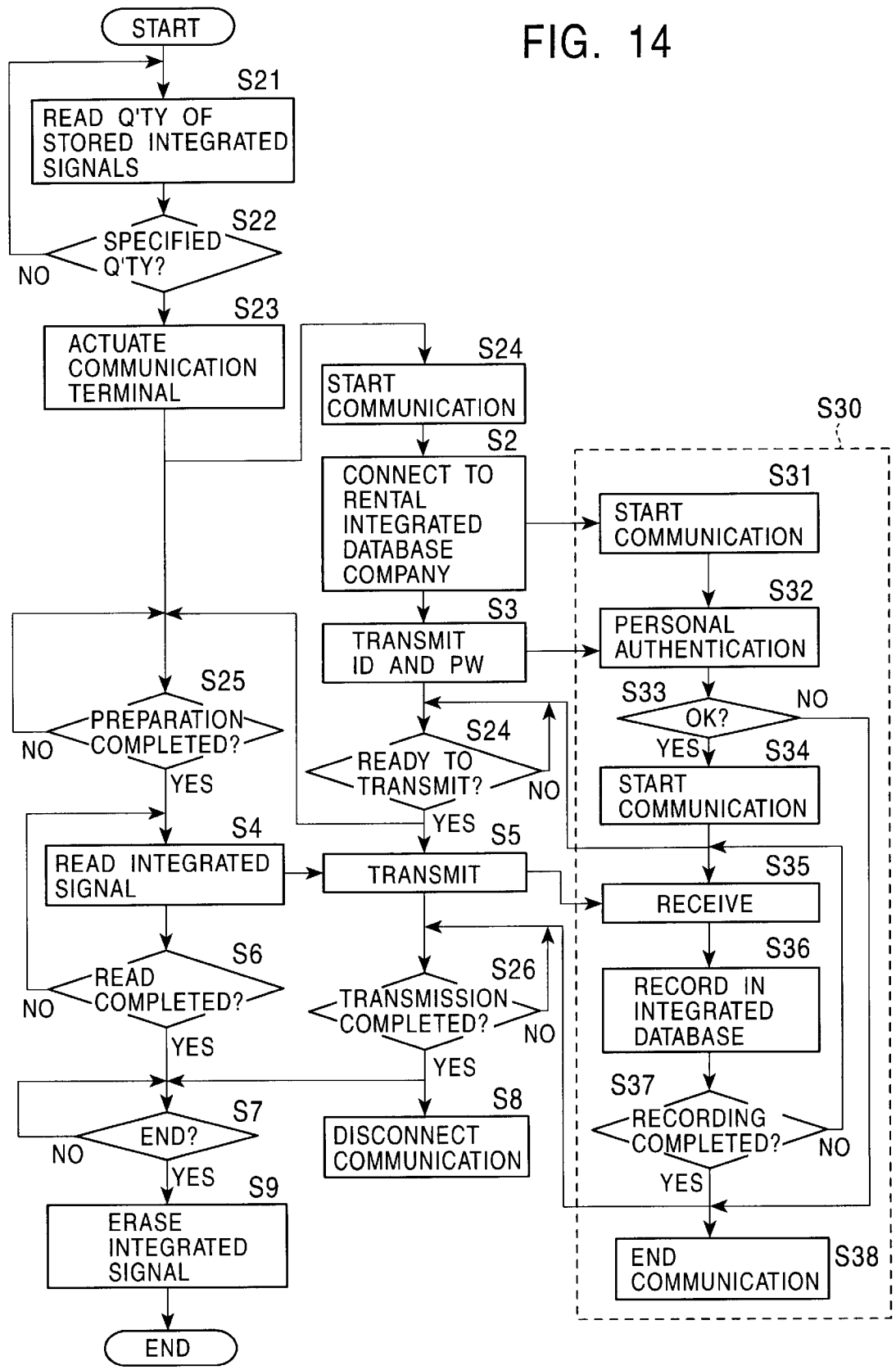
FIG. 14 is a flowchart for describing yet another example of the processing for transmitting data from the signal acquirer to the rental integrated database.

FIG. 14 shows the flowchart of another example of the procedure for transmitting data from the signal acquiring unit 1 to the rental integrated database 6. The processing shown in FIG. 14 indicates that an integrated signal is automatically transmitted to the rental integrated database 6 when the quantity of integrated signals stored in the storage 3 reaches a predetermined value. First, the quantity of stored integrated signals is read in step S21, then it is determined in step S22 whether the quantity has reached the predetermined value.

If it is determined in step S22 that the quantity has reached the predetermined value, then the communication terminal is actuated in step S23. This causes the communication to be started in step S24, and the connection to the rental integrated database 6 is made in step S2. As shown by S30, the processing carried out by the rental integrated database 6 is identical to that shown in FIG. 12 or FIG. 13. An ID and a password are transmitted from the actuated communication terminal 4, and it is determined in step S24 whether the preparations for transmission have been completed.

When the communication terminal 4 is ready for transmission and if it is determined in step S25 that the preparations of the storage 3 have been completed, then an integrated signal is read in step S4 and transmitted by the communication terminal 4 in step S5. If it is determined in step S26 that the transmission has been terminated, then the communication is cut off in step S8.

If it is determined in step S6 that the reading of the integrated signal has been terminated, then it is further determined in step S7 whether the reading and the transmission have been terminated. If the determination result is affirmative, then the integrated signal is deleted in step S9.

FIG. 15 exemplifies the attribute data included in the integrated signals registered in the individual databases of the rental integrated database 6. In the example shown in FIG. 15, a personal ID 100a, an event name 100b, a time stamp 100c, a location 100d, information 100e of link destination 1, and information 100f of link destination 2 are set as the attribute data. A reserve region is prepared for the attribute data so as to allow information at a link destination to be added or an additional category to be defined. The information at a link destination is required for the link to another database within the public database 7.

A linking method will now be described in conjunction with the specific example of attribute data shown in FIG. 16. In this example, the personal ID 100a is "TOKKYO TARO", the event name 100b is "WATCHING THE OPENING CEREMONY OF SYDNEY OLYMPIC", the time stamp 100c is "10:00 AM SEPT. 15, 2000", the location 100d is "OLYMPIC STADIUM", the information 100e of link destination 1 is "ABC BROADCAST MATERIAL NO. ???", and information 100f of link destination 2 is "NNS BROADCAST MATERIAL NO. XXX". This attribute data indicates the integrated signal representing the experience of a user named TOKKYO TARO at the opening ceremony of the Olympic. It is also shown that the material for broadcasting the opening ceremony is stored at, for example, a broadcast station "ABC" or "NNS" and has been opened to the public as public data.

As described above, the company managing the rental integrated database 6 searches for associated information from the public database 7 on the basis of the attribute data registered in the database. Then, based on the search result, the company writes the information at the link destination into the attribute data. In the foregoing example, the location where the broadcast station ABC or NNS stores the data regarding the Olympic opening ceremony is extracted from the public database 7 that has been opened to the public, and the storage location is automatically written to the information 100e and 100f indicating the link destinations in the attribute data.

Then, as mentioned above, the link to the public database 7 is established to acquire the data associated with the integrated signal already stored in the database of the rental integrated database 6 from the public database 7 so as to rewrite the integrated signal that has been registered in the database. By Such processing, in the information stored in the database of the rental integrated database 6, the information acquired from the public database is added to the information acquired by a user in the signal acquiring unit 1. This adds to the stock of data and also improves the quality thereof registered in the databases. In the foregoing example, the images and sounds collected by the broadcast stations will be registered in the database in addition to the images and sounds of the opening ceremony acquired by the user himself or herself.

Figure 17:
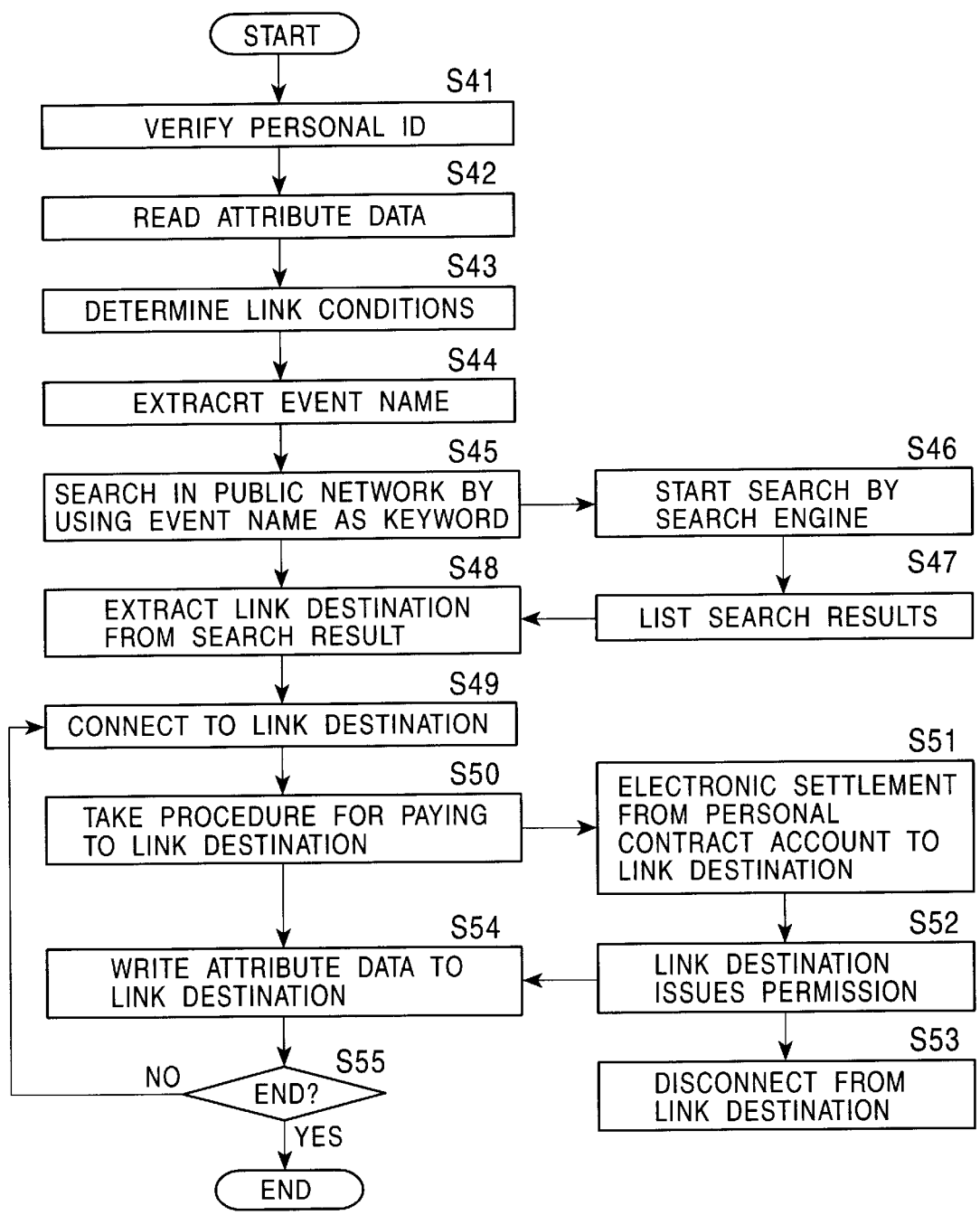
FIG. 17 is a flowchart for describing the operation of a rental integrated database in the embodiment of the present invention.

FIG. 17 shows a flowchart for explaining the search and automatic linking operation performed by the rental integrated database 6. The company managing the rental integrated database runs an automatic linking program according to a contract with or a request from a user. First, in step S41, the program reads particular data regarding the contractor from the database to verify a personal ID. Then, the program reads attribute data in step S42 to determine, in step S43, the linking conditions specified by the user beforehand, and extracts an event name from the determination result in step S44. In this case, a link destination may alternatively be decided from other information, such as a time stamp, in the attribute data.

In step S45, the database 7 in the open public network is searched, using the extracted event name as the keyword. The search is started by using a search engine in step S46, and search results are listed in step S47. In step S48, a predominant link destination is extracted from the listed search results.

Subsequently, the procedure for paying to the link destination is begun. The connection to the link destination is made in step S49, and the procedure for the payment to the link destination is carried out in step S50. The payment to the link destination is accomplished in step S51 through, for example, the public network 5, by electronic settlement from a personal account registered at the company managing the rental integrated database. This payment is an initial one-time payment, such as a membership fee or a deposit, that is irrespective of the amount of downloaded data.

When the link destination acknowledges the payment, a permission for the linking is issued in step S52. Upon verification of the permission, the connection to the link destination is made in step S52, and the information at the link destination is written into the attribute data in step S54. In step S55, it is determined whether the processing on the link destination, which has been extracted in step S48, has been completed. When the processing has been completed, the program is terminated.

Figure 18:
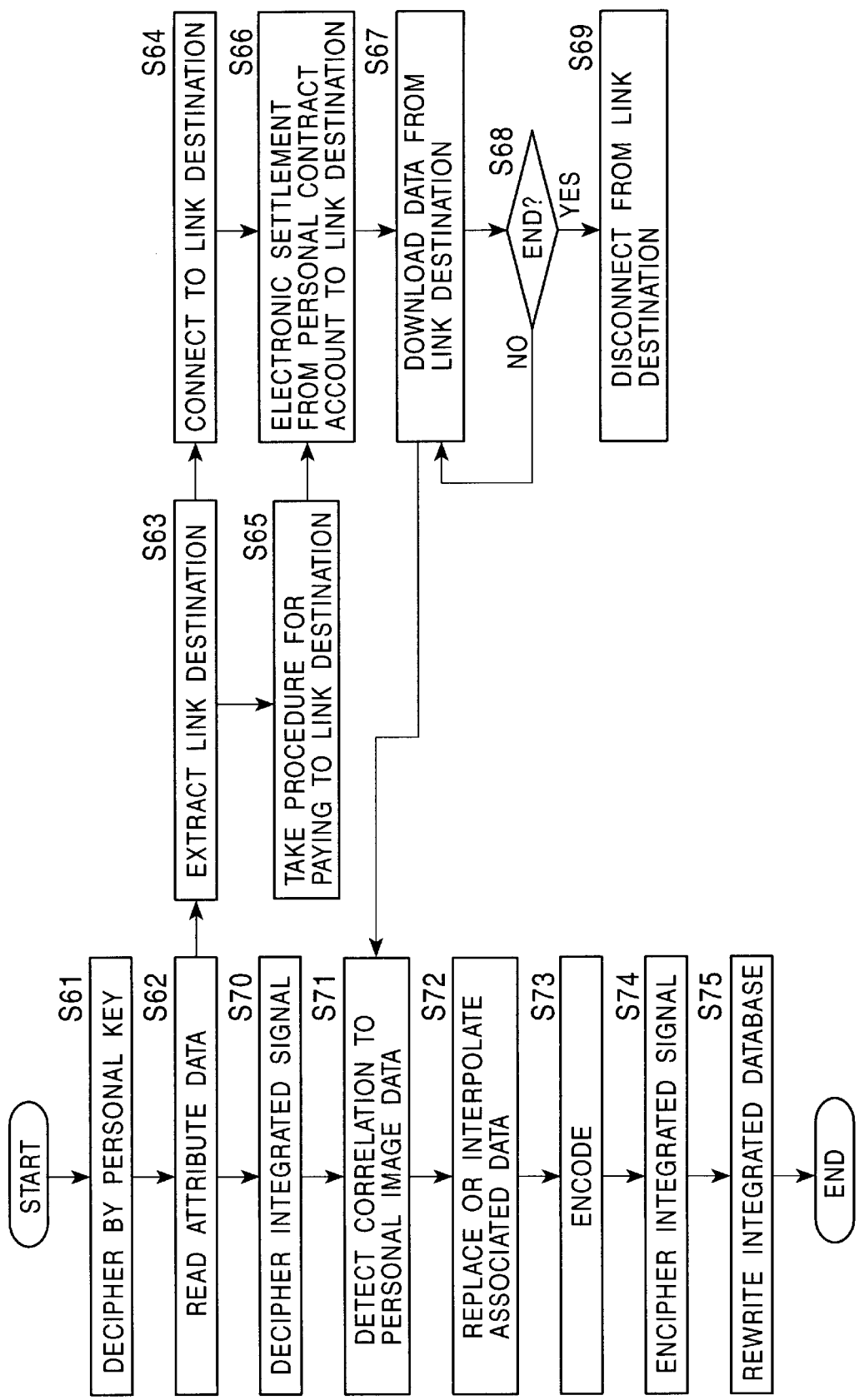
FIG. 18 is a flowchart for describing the operation of the rental integrated database in the embodiment of the present invention.

As discussed above, after the search of the automatically linked destination and the editing of the attribute data are completed, the automatic editing of the database contained in the rental integrated database is performed. FIG. 18 shows the flowchart illustrating the flow of the processing for automatically editing the contents of the integrated database. The company managing the rental integrated database runs an automatic editing program. First, integrated signal data is deciphered by using a personal key in step S61, then attribute data is read in step S62.

The information at a link destination is extracted from the attribute data in step S63. Based on the information, the rental integrated database 6 is connected to the link destination of the public database 7, e.g., a database of a broadcast station, in step S64. The procedure for paying the extracted link destination is carried out in step S65. In step S66, the payment to the link destination is accomplished through the public network 5 by electronic settlement from a personal account registered at the company managing the rental integrated database. In step S67, the data at the link destination is downloaded. The payment is based on the amount of downloaded data, meaning that the user is charged on an as-used basis. It is determined in step S68 whether the downloading has been completed, and if the determination result is affirmative, then the connection to the link destination is discontinued in step S69.

The integrated signals corresponding to the attribute data read in step S62 are deciphered and the integrated signals are separated into image data, audio data, bio-signals, etc. in step S70. Subsequently, in step S71, the program detects correlation in contents between the data downloaded from the link destination, such as image data, and the deciphered personal image data. Based on the correlation between the personal image data and the downloaded image data (the correlation in contents), replacement or interpolation or addition of images and/or sounds is carried out in step S72. Upon completion of automatic editing, all pieces of data are integrated by integrating and encoding again in step S73, and are enciphered again by using the personal key in step S74. In step S75, the database is rewritten by the enciphered, edited integrated signals, and the program is terminated.

Figure 19:
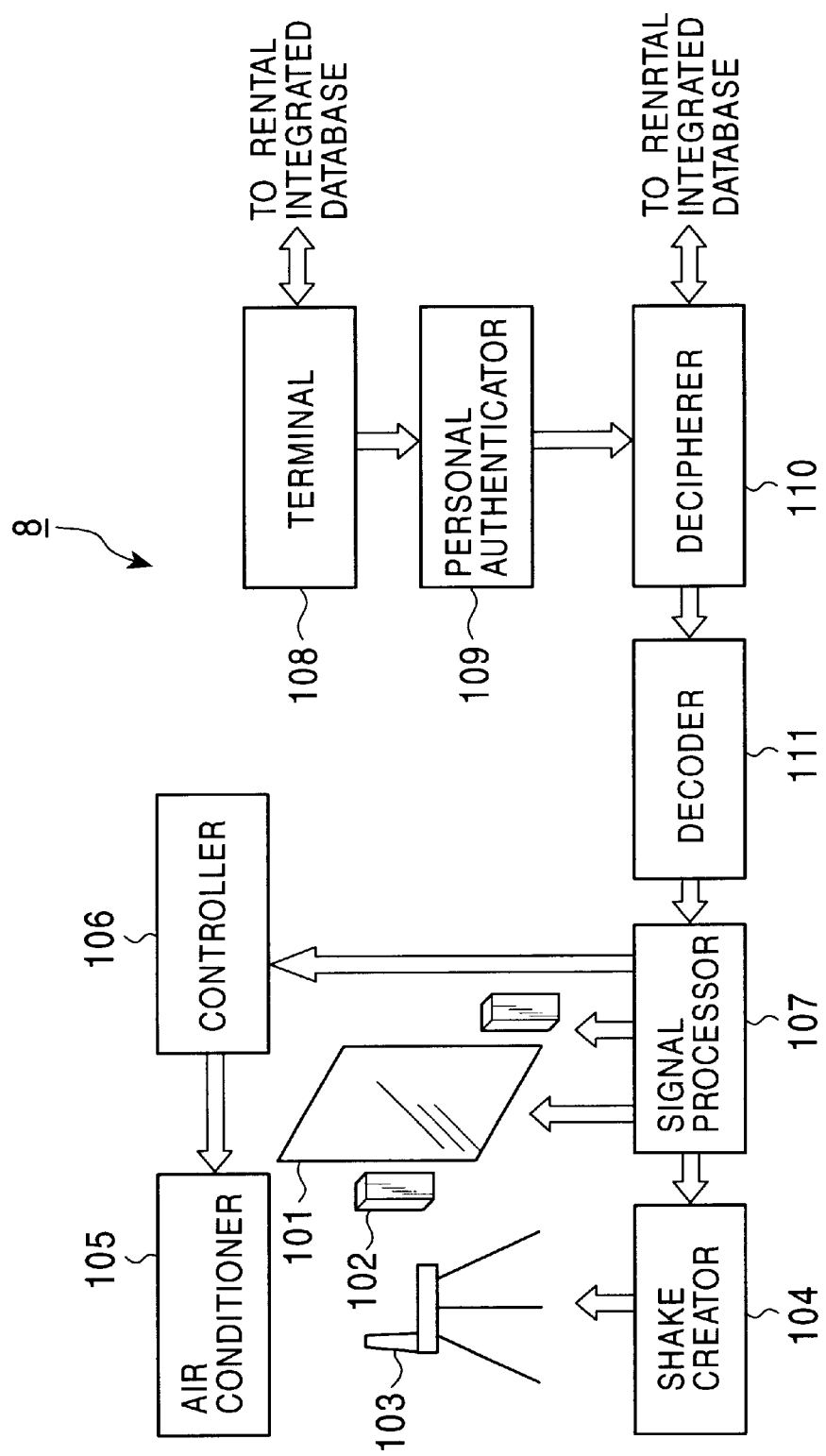
FIG. 19 is a block diagram showing the configuration of an example of an integrated signal presenting apparatus according to an embodiment of the present invention.

FIG. 19 shows the configuration of an example of the integrated signal presenter 8 that is connected to the rental integrated database 6 and installed at a re-experience center. The presenter 8 is installed at the re-experience center, so that a user may visit the re-experience center to have a re-experience when the user wishes to have an experience that he or she has had in the past.

The integrated signal presenter 8 includes a screen 101 for providing a large screen at the front and a three-dimensional acoustic device 102 in a special room where air conditioning, including temperature and humidity, can be controlled. In the example shown in FIG. 19, the screen 101 has one surface; however, it may alternatively be an immersion type screen having a front, right, and left screen faces. Images are projected onto the screen 101 by a reflection type or transmissive type projector. The acoustic device 102 may reproduce sounds through the screen 101 or perform sound field reproduction through many speakers embedded in a wall.

A moving chair 103 is installed at the center of the room. The chair 103 is designed to be movable in three-dimensional directions and driven by an output of a shake creator 104. The shake creator 104 detects a motion vector from an image signal among integrated signals, and creates a shake signal component based on the detected motion vector. The shake creator 104 is equipped with a storage device, such as a hard disk, for storing shake signals. The moving chair 103 makes it possible to reproduce vibrations felt when, for example, walking, running, or driving. An example of the method for generating such shake signals is disclosed in, for example, U.S. patent application Ser. No. 09/488286.

An air conditioner 105 mainly controls the temperature and humidity in the room, and is controlled by a controller 106. The controller 106 is provided with a storage, such as a hard disk, for storing control data. The screen 101 and the acoustic device 102 serving as the image reproducing unit described above is controlled by a signal processor 107. The signal processor 107 is equipped with a storage, such as a hard disk, for storing image data and acoustic data.

The presenter 8 includes a terminal 108, a personal authenticator 109, a decipherer 110, and a decoder 111 to receive integrated signals from the rental integrated database 6 and to decipher and decode the received signals. Integrated signals from the decoder 111 are supplied to the signal processor 107, and control signals for the above devices are generated by the signal processor 107 on the basis of the integrated signals. The signal processor 107, the terminal 108, the personal authenticator 109, the decipher 110, and the decoder 111 are formed mainly by a workstation in practical use, and installed at a corner of the room.

Figure 20:
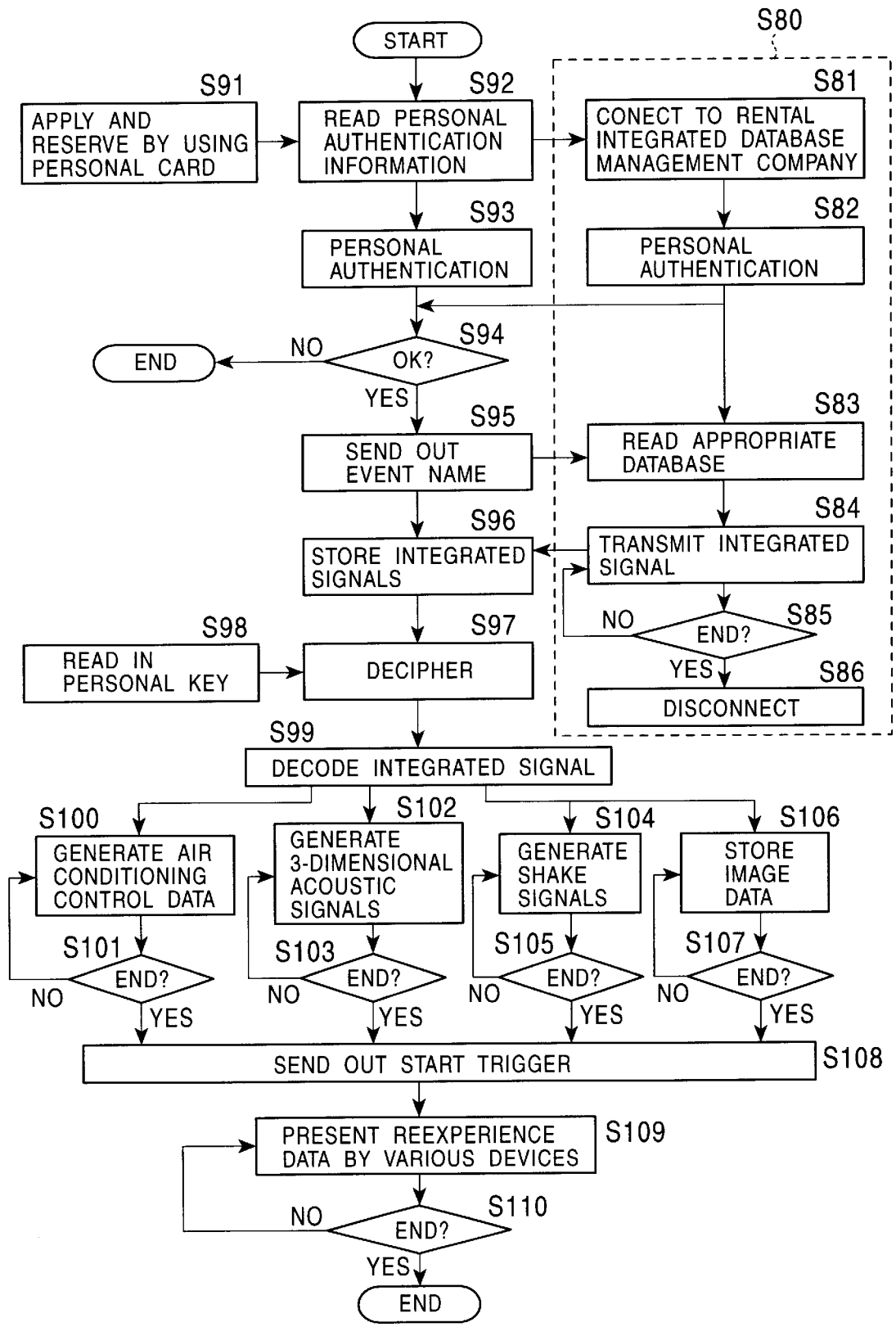
FIG. 20 is a flowchart for describing the operation of the integrated signal presenting apparatus according to an embodiment of the present invention.

FIG. 20 shows a flowchart illustrating the flow of a series of operations associated with the integrated signal presenter 8. When a user decides that he or she wants to have a re-experience, the user visits the re-experience center and takes a predetermined procedure at a ticket booth of the center. The predetermined procedure includes applying for a re-experience by using a user-specific card and paying for the use of the integrated signal presenter 8 by electronic settlement. The user-specific card is made of, for example, an IC card in which an ID unique to a user, the information regarding an account for electronic settlement, and other information have been recorded by being enciphered using bio-data (fingerprints or the like) as a key. The user presents the user-specific card at the ticket booth and performs personal authentication thereby to make a reservation for an event the user wishes to re-experience and also to complete the procedure for the electronic settlement in step S91.

When the reserved time is reached, the user enters the room of the integrated signal presenter 8 and sits on the moving chair 103. This starts a re-experience program. First, in step S92, the personal authentication information is read. Then, in step S81, the terminal 108, which is a part of the integrated signal presenter 8, connects to the company managing a rental integrated database through the intermediary of a network.

Based on the personal authentication information and the name of an event to be re-experienced that have been already entered at the ticket booth, the personal authentication is performed in steps S82 and S93, and it is determined in step S94 whether the authentication is successful. If the determination result is negative, then the processing terminates at that point. If the determination result is affirmative, then the event name is transmitted to the rental integrated database 6 in step S95.

In step S83, the rental integrated database 6 starts reading and downloading the integrated signal data. In FIG. 20, the processing of S80 enclosed by a dashed line is the processing carried out by the rental integrated database 6. In step S84, integrated signals are transmitted to the integrated signal presenter 8. In step S85, the completion of the transmission is monitored, and the connection is discontinued in step S86 upon completion of the transmission.

The integrated signal presenter 8 stores the received integrated signals in step S96. Then, the integrated signals are deciphered in step S97 according to a personal key, e.g., a bio-signal key, such as fingerprint information, that has been read in step S98. Subsequently, the integrated signals are decoded in step S99 thereby to separate the original image data, audio data, diverse bio-signals, etc.

Based on the signals of the temperature sensor and the perspiration sensor or the like among the bio-signals, control data for controlling the air conditioner 105 is generated in step S100. In step S101, it is determined whether the generation of the air conditioning control data has been completed. The air conditioning data is used to presumed the ambient temperature and humidity at the time of the experience, and an operation programming that includes the time-dependent changes of the air conditioner is effected.

Based on the decoded audio signals, three-dimensional acoustic signals are generated in step S102. In step S103, it is determined whether the generation of the acoustic signals has been completed. Conversational voices, surrounding sounds, and the like are reproduced by the acoustic signals.

In step S104, shake signals are produced on the basis of the decoded image signals. Motion vectors of the image signals are detected, and the shake signals are produced on the basis of the detected motion vectors. In step S105, it is determined whether the generation of the shake signals has been completed. In step S106, the decoded image signals are stored. In step S107, it is determined whether storing the image signals has been completed.

When the completion of the processing is detected in steps S101, S103, S105, and S107, the program stands by until all data is supplied. When all data is received, the trigger signal for starting an operation is sent out from the signal processor 107 to the shake creator 104 and the controller 106 in step S108. In step S109, the trigger signal brings about synchronization, and the presentation of all data is begun. This provides realism-enhanced reproduction of the event experienced in the past. Moreover, experiences with improved realistic somesthetic effect are achieved by the supplement of high-quality data, such as broadcast materials or the like, obtained from a public database. Upon completion of the reproduction of the series of data for the re-experience, the program is terminated.

The present invention is not limited to the embodiment or the like in accordance with the invention described above. To the contrary, the invention is intended to cover various modifications and equivalent arrangements included within the spirit and scope of the invention. For example, in the integrated signal presenter 8, the processing for generating air conditioning control data, acoustic signals, shake signals, etc. and the processing for storing image signals may be carried out beforehand after a user makes a reservation, so that the user can start a re-experience with a shorter waiting time. As another alternative, a user may receive attribute data from a rental integrated database so as to edit or process the attribute data by himself or herself.

As described above, according to the present invention, the audiovisual signals and bio-signals produced when a user actually has an experience are acquired, and impressive signals among the acquired signals are selectively stored by using bio-information. Furthermore, according to the present invention, the audiovisual signals and bio-signals are stored in a database, allowing reproduction accompanied by somesthetic effect to be achieved for a re-experience. This makes it possible to achieve a re-experience with rich realism that cannot be accomplished by photographs or video data. Moreover, according to the present invention, associated information can be acquired from an external database in addition to the data acquired by a person so as to supplement the contents of a database, thus enabling the database to have a better stock of contents with higher quality.

What is claimed is:

1. A signal acquiring apparatus comprising:
   a plurality of sensors attached to a person, said plurality of sensors including at least one biometric sensor to sense bio-information of the person and at least one audio/video sensor to sense audio/video perceivable by the person in the person's environment;
   detecting means for generating detection signals from the at least one biometric sensor;
   selecting means for automatically selecting detection signals containing effective information from among the detection signals generated by said at least one biometric sensor; and
   storing means for storing the selected detection signals, and for storing audio/video from said audio/video sensor perceived by the person when said detection signals containing said effective information are selected;

wherein said audio/video includes audio/video signals of the audio/video perceived by the person that correlated with a change in said bio-information, to enable a subsequent re-experience by the person when the audio/video signals are reproduced in the person's presence.

2. The signal acquiring apparatus according to claim 1, further comprising:

encoding means for encoding the plurality of detection signals so that they are integrated, wherein the encoded detection signals are stored in the storing means.

3. The signal acquiring apparatus according to claim 1, wherein attribute data is added to the detection signals so as to allow the detection signals to be identified by the attribute data.

4. The signal acquiring apparatus according to claim 1, wherein the detecting means is portable.

5. The signal acquiring apparatus according to claim 1, wherein a detection signal from the detecting means is transmitted to the storing means through the intermediary of a recording medium or communication.

6. A database comprising:

means for receiving detection signals from each of a plurality of sensors attached to a person and stored at a storing means, said plurality of sensors including at least one biometric sensor to sense bio-information of the person and at least one audio/video sensor to sense audio/video perceivable by the person in the person's environment;

storage means for each person, in which received detection signals associated with the person are stored, and for storing audio/video from said audio/video sensor perceived by the person when said detection signals containing effective information are selected;

communication means that is connected to an external database to access information in another database associated with the stored detection signals; and means for acquiring associated information from the another database via the communication means;

wherein said audio/video includes audio/video signals of audio/video perceived by the person that correlated with a change in said bio-information, to enable a subsequent re-experience by the person when the audio/video signals are reproduced in the person's presence.

7. The database according to claim 6, wherein attribute data added to the detection signals so as to identify the detection signals is stored.

8. The database according to claim 6, wherein the storage means for each person is rented out to a registered user.

9. A database system comprising:

a signal acquiring apparatus having a plurality of sensors attached to a person, detecting means for generating detection signals from the at least one biometric sensor, selecting means for automatically selecting detection signals containing effective information from among the detection signals generated by said at least one biometric sensor, and storing means for storing the selected detection signals, and for storing audio/video from said audio/video sensor perceived by the person when said detection signals containing said effective information are selected, wherein said plurality of sensors include at least one biometric sensor to sense bio-information of the person and at least one audio/video sensor to sense audio/video perceivable by the person in the person's environment; and a database connected to the signal acquiring apparatus through the intermediary of communication means, wherein the database comprises means for receiving detection signals from the signal acquiring apparatus and storage means for each person, in which the received detection signals are stored, and for storing audio/video from said audio/video sensor perceived by the person when said detection signals containing said effective information are selected;

wherein said audio/video includes audio/video signals of audio/video perceived by the person that correlated with a change in said bio-information, to enable a subsequent re-experience by the person when the audio/video signals are reproduced in the person's presence.

10. The database system according to claim 9, further comprising:

communication means that is connected to an external database to access information in another database associated with the stored detection signals; and means for acquiring associated information from the another database via the communication means.

11. A signal presenting system comprising:

a database having means for receiving detection signals from each of a plurality of sensors attached to a user, said plurality of sensors including at least one biometric sensor to sense bio-information of the person and at least one audio/video sensor to sense audio/video perceivable by the person in the person's environment, and storage means for each person in which received detection signals are stored for each user, and for storing audio/video from said audio/video sensor perceived by the person when said detection signals containing effective information are selected; and a signal presenting apparatus connected to the database via a communication means, wherein the signal presenting apparatus includes means for receiving detection signals from the database via the communication means, and means for reproducing an environment on the basis of the detection signals; and said audio/video includes audio/video signals of audio/video perceived by the person that correlated with a change in said bio-information, to enable a subsequent re-experience by the person when the audio/video signals are reproduced in the person's presence.

12. A signal acquiring, storing, and presenting system comprising:

a signal acquiring apparatus that has a plurality of sensors attached to a person, said plurality of sensors include at least one biometric sensor to sense bio-information of the person and at least one audio/video sensor to sense audio/video perceivable by the person in the person's environment, detecting means for generating detection signals from the at least one biometric sensor, selecting means for automatically selecting detection signals containing effective information from among the detection signals generated by said at least one biometric sensor, and storing means for storing the selected detection signals, and for storing audio/video from said audio/video sensor perceived by the person when said detection signals containing said effective information are selected;

a database including means that is connected to the signal acquiring apparatus via first communication means to receive detection signals from the signal acquiring apparatus and storage means for each person in which the received detection signals are stored for each user; and a signal presenting apparatus including means that is connected to the database via second communication means to receive detection signals from the database, and means for reproducing an environment on the basis of the detection signals;

wherein said audio/video includes audio/video signals of audio/video perceived by the person that correlated with a change in said bio-information, to enable a subsequent re-experience by the person when the audio/video signals are reproduced in the person's presence.

13. A signal acquiring, storing, and presenting system comprising:

a first manager that manufactures and/or markets a signal acquiring apparatus having a plurality of sensors attached to a person, plurality of sensors include at least one biometric sensor to sense bio-information of the person and at least one audio/video sensor to sense audio/video perceivable by the person in the person's environment, detecting means for generating detection signals from the at least one biometric sensor, selecting means for automatically selecting detection signals containing effective information from among the detection signals generated by said at least one biometric sensor, and a storing means for storing the selected detection signals, and for storing audio/video from said audio/video sensor perceived by the person when said detection signals containing said effective information are selected;

a second manager that manages a database including a means that is connected to the signal acquiring apparatus via first communication means to receive detection signals from the signal acquiring apparatus and storage means for each person, in which the received detection signals associated with the person are stored; and a third manager that manages a signal presenting apparatus including means that is connected to the database via second communication means to receive detection signals from the database, and means for reproducing an environment on the basis of the detection signals;

wherein said audio/video includes audio/video signals perceived by the person that correlated with a change in said bio-information, to enable a subsequent re-experience by the person when the audio/video signals are reproduced in the person's presence.

14. The signal acquiring, storing, and presenting system according to claim 13, wherein the first manager is separated into a manager that manufacturers and/or markets the detecting means and a manager that manufactures and/or markets the selecting means and the storing means.

15. A signal acquiring method comprising a plurality of sensors attached to a person, said plurality of sensors including at least one biometric sensor to sense bio-information of the person and at least one audio/video sensor to sense audio/video perceivable by the person in the person's environment, said signal acquiring method comprising the steps of:

generating detection signals from the at least one biometric sensor;

automatically selecting detection signals containing effective information from among the detection signals generated by said at least one biometric sensor; and storing the selected detection signals, and storing audio/video from said audio/video sensor perceived by the person when said detection signals containing said effective information are selected;

wherein said audio/video includes audio/video signals of the audio/video perceived by the person that correlated with a change in said bio-information, to enable a subsequent re-experience by the person when the audio/video signals are reproduced in the person's presence.

16. The signal acquiring method according to claim 15, further comprising the step of:

encoding the plurality of detection signals so that they are integrated, wherein the encoded detection signals are stored.

17. The signal acquiring method according to claim 15, wherein attribute data is added to the detection signals so as to allow the detection signals to be identified by the attribute data.

18. The signal acquiring method according to claim 15, wherein the detection signals are stored in a portable device.

19. The signal acquiring method according to claim 15, wherein a detection signal is transmitted through the intermediary of a recording medium or communication.

* * * * *